United States Patent [19]

Willms et al.

[11] Patent Number: 4,718,937
[45] Date of Patent: Jan. 12, 1988

[54] N-ALKOXYAMINOSULFONYLUREAS AND N-ALKYLSULFONYLAMINOSULFONYLUREAS

[75] Inventors: Lothar Willms, Unkel; Hilmar Mildenberger, Kelkheim; Klaus Bauer, Rodgau; Helmut Bürstell, Frankfurt am Main, all of Fed. Rep. of Germany

[73] Assignee: Hoechst Aktiengesellschaft, Frankfurt am Main, Fed. Rep. of Germany

[21] Appl. No.: 849,737

[22] Filed: Apr. 9, 1986

Related U.S. Application Data

[62] Division of Ser. No. 627,763, Jul. 5, 1984, Pat. No. 4,601,747.

[30] Foreign Application Priority Data

Jul. 9, 1983 [DE] Fed. Rep. of Germany ....... 3324802

[51] Int. Cl.⁴ .................. C07D 251/52; C07D 251/46; A01N 43/66; A01N 43/70
[52] U.S. Cl. ........................................ 71/93; 544/213; 544/197; 544/199; 544/208; 544/210; 544/205; 544/206; 544/211; 544/7; 71/92
[58] Field of Search ............... 544/197, 199, 205, 206, 544/210, 208, 213, 211; 71/93

[56] References Cited

U.S. PATENT DOCUMENTS

| | | | |
|---|---|---|---|
| 4,440,565 | 4/1984 | Willms et al. | 544/199 |
| 4,492,598 | 1/1985 | Willms et al. | 544/208 |
| 4,534,790 | 8/1985 | Wolf | 544/212 |
| 4,592,776 | 6/1986 | Van Gemert | 544/211 |
| 4,601,747 | 7/1986 | Willms et al. | 544/194 |

*Primary Examiner*—John M. Ford
*Attorney, Agent, or Firm*—Curtis, Morris & Safford

[57] ABSTRACT

The compounds of the general formula (I)

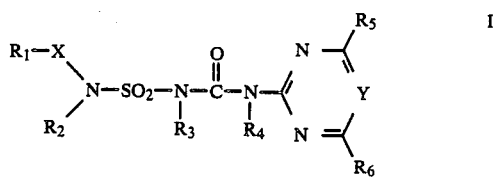

in which X denotes O or $-SO_2-$, Y denotes CH or N, $R_1$ denotes alkyl, alkenyl or $(C_2-C_6)$-alkinyl which are optionally substituted, $R_2$ denotes alkyl, alkenyl, alkinyl or cyclohexyl, $R_3$ and $R_4$ denote H or alkyl, and $R_5$ and $R_6$ denote H, (substituted) alkyl, (substituted) alkoxy, halogen, alkylthio, monoalkylamino or dialkylamino, and also salts thereof, possess advantageous herbicidal properties against monocotyledonous and dicotyledonous weeds and are suitable for selective use in large-scale crops. In addition, they possess a good plant growth-regulating action.

4 Claims, No Drawings

N-ALKOXYAMINOSULFONYLUREAS AND N-ALKYLSULFONYLAMINOSULFONYLUREAS

This application is a division of application Ser. No. 627,763, filed July 5, 1984, now U.S. Pat. No. 4,601,747.

It is already known that phenylsulfonylureas containing heterocyclic substituents exhibit herbicidal or plant growth-regulating properties, cf., for example, Netherlands Pat. No. 121,788, German Offenlegungsschrift No. 2,715,786 and European Pat. No. 1,485.

However, these compounds exhibit disadvantages in use, such as, for example, high persistence or inadequate selectivity.

It has now been found that N-alkoxyaminosulfonylureas and N-alkylsulfonylaminosulfonylureas which have heterocyclic substituents and which contain, as the heterocyclic component, a pyrimidine or triazine ring, are particularly suitable for use as herbicides and plant growth-regulators.

The present invention relates, accordingly, to the new compounds of the general formula (I)

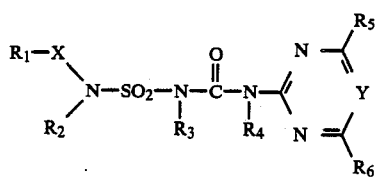

in which X denotes O or —$SO_2$—, Y denotes CH or nitrogen, $R_1$ denotes a ($C_1$–$C_6$)-alkyl, ($C_2$–$C_6$)-alkenyl or ($C_2$–$C_6$)-alkinyl radical which are optionally substituted by halogen, ($C_1$–$C_4$)-alkoxy or ($C_1$–$C_4$)-alkoxycarbonyl, $R_2$ denotes hydrogen, ($C_1$–$C_6$)-alkyl, ($C_2$–$C_6$)-alkenyl, ($C_2$–$C_6$)-alkinyl or cyclohexyl, $R_3$ and $R_4$ independently of one another denote hydrogen or ($C_1$–$C_4$)-alkyl, and $R_5$ and $R_6$ independently of one another denote hydrogen, ($C_1$–$C_4$)-alkyl or ($C_1$–$C_4$)-alkoxy which both can optionally be monosubstituted or polysubstituted by halogen, ($C_1$–$C_4$)-alkoxy or ($C_1$–$C_4$)-alkylthio, or denote halogen, ($C_1$–$C_4$)-alkylthio, ($C_1$–$C_4$)-alkylamino or ($C_1$–$C_4$)-dialkylamino, and also, if $R_2$ and $R_3$ denote hydrogen, physiologically acceptable salts thereof with bases.

"Halogen" preferably denotes fluorine, chlorine or bromine.

Amongst the compounds of the formula I preferred compounds are those in which $R_1$ and $R_2$ independently of one another denote ($C_1$–$C_3$)-alkyl or ($C_1$–$C_3$)-alkenyl, $R_3$ and $R_4$ denote hydrogen, $R_5$ and $R_6$ independently of one another denote ($C_1$–$C_2$)-alkyl or ($C_1$–$C_2$)-alkoxy, x denotes $SO_2$ and Y denotes CH.

The invention also relates to new (pyrimidino) triazinothiadiazine oxides of the formula (II) which, as stated below, can act as intermediates for the preparation of the compounds, according to the invention, of the formula (I).

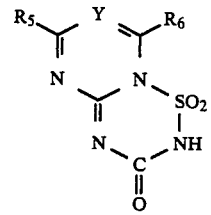

The new compounds of the formula I can be synthesized from starting materials which are known per se or have been prepared by known processes.

Processes of preparation comprise:

(a) reacting compounds of the formula (III)

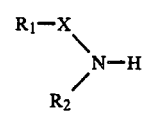

in which $R_1$, $R_2$ and X have the abovementioned meanings, with compounds of the formula (IV)

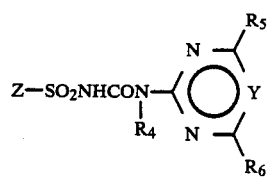

in which Z denotes fluorine, chlorine or ($C_1$–$C_4$)-alkoxy or phenoxy which are optionally halogenated, especially chlorine, and $R_4$, $R_5$, $R_6$ and Y correspond to the definitions employed for the compounds of the formula (I), or (b) reacting compounds of the formula (II)

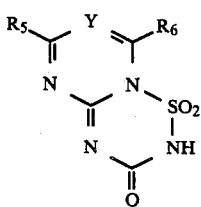

in which Y, $R_5$ and $R_6$ correspond to the definitions employed for compounds of the formula (I), with compounds of the abovementioned formula (III), or (c) in the event that X=$SO_2$, reacting compounds of the formula (V)

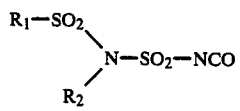

in which $R_1$ and $R_2$ correspond to the definitions given for compounds of the formula (I), with compounds of the formula (VI)

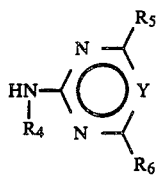

in which $R_4$, $R_5$, $R_6$ and Y have the abovementioned meanings, and, if appropriate, alkylating the compounds of the formula (I) obtained in accordance with (a) to (c) in which $R_2$ and $R_3$ independently of one another denote hydrogen, in the $R_2$-position or $R_3$-position.

In regard to (a); the reaction of the compounds (III) and (IV) is preferably carried out in inert aprotic solvents, such as aliphatic or aromatic hydrocarbons, in particular n-hexane, toluene or xylene, acetonitrile, methylene dichloride, chloroform, nitromethane, tetrahydrofuran or dioxane, at temperatures between −78° C. and the boiling point of the solvent, preferably in the presence of an acid acceptor, such as a tertiary organic amine, in particular pyridine or triethylamine, or an inorganic base, such as an alkali metal carbonate. In the event that X=oxygen, the compounds (III) can, if desired, be employed in excess in order to act as an auxiliary base at the same time.

In regard to (b); in the reaction of the compounds (II) and (III) it is preferable to use the same solvents as in (a) and to carry out the reaction at temperatures between −78° C. and the boiling point of the solvent. If appropriate, the reaction is carried out with the addition of one or more equivalents of basic compounds, such as tertiary organic amines, in particular triethylamine, ethyldiisopropylamine or pyridine, or inorganic bases, such as potassium carbonate.

In regard to (c); the acylation of amino-heterocyclic compounds of the formula VI with sulfonyl isocyanates of the formula V is preferably also carried out in the same solvents as those mentioned under (a) at temperatures between −20° C. and the boiling point of the solvent.

The subsequent alkylation of the compounds of the formula I in the $R_2$-position or $R_3$-position is preferably carried out in inert solvents, such as, for example, dioxane or dimethylformamide, with the addition of an inorganic base, such as sodium hydride or potassium carbonate, at temperatures from 0° C. up to the boiling point of the solvent. The alkylating agents employed are customary agents, such as dimethyl sulfate, methyl iodide or ethyl bromide.

Compounds of the formula I in which $R_2$ or $R_3$ denotes hydrogen can form salts in which H is replaced by a suitable cation. These salts are, in general, metal salts, in particular alkali or alkaline earth metal salts, or optionally alkylated ammonium salts or organic amine salts, and are preferably prepared in inert solvents, such as, for example, water, methanol or acetone, at temperatures from 20° to 100° C. Examples of suitable bases for the preparation of the salts according to the invention are alkali metal carbonates, ammonia or ethanolamine.

The starting materials of the formula (II) required for the preparation of the compounds, according to the invention, of the formula (I) are new and can be prepared by carrying out an addition reaction between chlorosulfonyl or fluorosulfonyl isocyanate and amino-heterocyclic compounds of the abovementioned formula (VI) in the presence of bases, such as tertiary organic amines, in particular triethylamine or ethyldiisopropylamine. The compounds of the formula II and the process for preparing them are therefore also a part of the invention. This process is preferably carried out in inert organic solvents, such as methylene dichloride, acetonitrile or tetrahydrofuran, at temperatures between −78° C. and +40° C. Owing to low yields, this method of preparing the compounds of the formula II is less suitable when $R_5$ and $R_6$ are $(C_1-C_4)$-alkylamino or $(C_1-C_4)$-dialkylamino. In the process of preparation mentioned, the compounds of the formula II are obtained in the form of mixtures of isomers in the event that $R_5 \neq R_6$. These are mixtures of two positions isomers, the meanings of $R_5$ and $R_6$ being exchanged in the two isomers, since the cyclization of the sulfonyl group of the halogenosulfonyl isocyanate can take place at either of the nitrogen atoms of formula VI adjacent to the amino group. These mixtures of regio-isomers can be separated by customary methods, such as recrystallization, chromatography and the like.

The starting materials of the formula III are known or can be prepared by processes which are known in principle. The corresponding hydroxylamines of the formula (III) (X=O) are prepared, for example, by alkaline hydrolysis of alkylalkoxycarbamic acid esters, cf. Angew. 75, 851 (1963).

The aliphatic sulfonamides of the formula (III) (X=SO$_2$) can be prepared, for example, from alkylsulfochlorides by reacting the latter with primary aliphatic amines.

The heterocyclic sulfonylureas of the formula (IV) are known or can be prepared by known methods, in the case of Z=chlorine cf. European Pat. No. 39,329, in the case of Z=alkoxy cf. European Patent Application No. 61,611 and in the case of Z=phenoxy cf. British Pat. No. 2,015,503.

The sulfonyl isocyanates of the formula (V) are prepared by reacting chlorosulfonyl isocyanate with secondary aliphatic sulfonamides (German Offenlegungsschrift No. 2,257,240).

The starting materials of the formula IV are known or can be prepared by processes which are known in principle, for example by cyclizing appropriate guanidine derivatives by means of appropriately substituted 1,3-di-ketones, cf., for example, "The Chemistry of Heterocyclic Compounds", volume XVI (1962) and Supplement I (1970), or by preparing derivatives of cyanuric chloride, cf., for example, "The Chemistry of Heterocyclic Compounds", L. Rapoport: "s-Triazines and Derivatives" (1959).

The heterocyclic sulfonylurea derivatives according to the invention exhibit an excellent herbicidal action and a very good selectivity in important large-scale crops. They are therefore suitable for the selective control of dicotyledonous and grass-like annual and perennial weeds, especially in crops of agricultural importance, such as, for example, wheat, barley, rye, rice, maize, sugar-beet and soya. It is immaterial in this respect whether the substances are applied by pre-sowing, pre-emergence or post-emergence spraying. If the compounds according to the invention are applied to the surface of the soil by the pre-sowing or pre-emergence technique before the weed plants have germinated, the emergence of the seedlings is not prevented. The weeds grow up to the cotyledon stage, but then cease their growth and finally wither completely after 3–5 weeks. If the active compounds are applied to the green parts of the plants by the post-emergence technique, a drastic cessation of growth also sets in very rapidly after the treatment, and the weed plants remain in the stage of growth existing at the time of application or wither completely after a certain time, so that weed competition harmful to the crop plants is eliminated in this way very soon and for an extended period.

In addition, the substances according to the invention exhibit outstanding growth-regulating properties in respect of crop plants. They intervene in a regulatory manner in the internal metabolism of the plants and can thus be employed for selectively influencing substances contained in plants and for facilitating harvesting, for example by initiating dessication and stunting of growth. Furthermore, they are also suitable for generally controlling and inhibiting undesirable vegetative growth without thereby destroying the plants. In the case of many monocotyledonous and dicotyledonous crops, inhibiting vegetative growth plays an important part, since it makes it possible to reduce or completely prevent lodging. The growth-regulating activity of the compounds as growth inhibitors in cereals, maize, soya, cotton and grass lawns should be singled out particularly, as should also their capacity to increase the content of desirable contained substances, such as carbohydrates and protein, in useful plants. Finally, the compounds exhibit a very good improvement in the abscission of fruit, particularly in the case of citrus fruits, or a reduction in retentive force.

The invention also relates, therefore, to herbicidal and growth-regulating agents which contain a compound of the formula I in combination with customary formulation auxiliaries and inert substances, and also to the use of the latter in the agricultural sector.

The agents according to the invention generally contain 2–95% by weight of the active compounds of the formula I. They can be used in the customary formulations as wettable powders, emulsifiable concentrates, sprayable solutions, dusting agents or granules.

The wettable powders are preparations which can be dispersed uniformly in water and which, in addition to the active compound, contain not only a diluent or inert substance but also a wetting agent, for example polyoxethylated alkylphenols, polyoxethylated fatty alcohols, alkylsulfonates or alkylphenylsulfonates, and a dispersing agent, for example sodium ligninsulfonate, sodium 2,2'-dinaphthylmethane-6,6'-disulfonate, sodium dibutylnaphthalenesulfonate or sodium oleylmethyltaurate.

Emulsifiable concentrates are prepared by dissolving the active compound in an organic solvent, for example butanol, cyclohexanone, dimethylformamide, xylene or higher-boiling aromatic compounds or hydrocarbons, with the addition of one or more emulsifiers. The following are examples of emulsifiers which can be used:

Calcium salts of alkylarylsulfonic acid, such as Ca dodecylbenzenesulfonate, or nonionic emulsifiers, such as polyglycol esters of fatty acids, alkylaryl polyglycol ethers, fatty alcohol polyglycol ethers, propylene oxide/ethylene oxide condensation products, fatty alcohol/propylene oxide/ethylene oxide condensation products, alkyl polyethers, fatty acid esters of sorbitan, fatty acid esters of polyoxethylenesorbitol or esters of polyoxethylenesorbitol.

Dusting agents are obtained by grinding the active compound with finely divided solid substances, for example talc, natural clays, such as kaolin, bentonite or pyrophillite, or diatomaceous earth.

Granules can be prepared either by atomizing the active compound onto an adsorbent, granulated inert material or by applying active compound concentrates by means of adhesives, for example polyvinyl alcohol, sodium polyacrylate or mineral oils, to the surface of carriers, such as sand, kaolinite or granulated inert material. Suitable active compounds can also be prepared in the manner customary for the preparation of fertilizer granules, if desired as a mixture with fertilizers.

In the case of herbicidal agents, the concentrations of active compound in the commercial formulations can vary.

In wettable powders, for example, the concentration of active compound varies between about 10% and 80%, the remainder is composed of the formulation additives indicated above. In emulsifiable concentrates, the concentration of active compound can also be about 10% to 80%. Formulations in the form of dusts contain about 2–20%. In granules, the content of active compound depends in part on whether the active compound is in a liquid or solid form and on the granulating auxiliaries, fillers and the like which are used.

For use as herbicides, the commercial concentrates are, if appropriate, diluted in a customary manner, for example by means of water in the case of wettable powders and emulsifiable concentrates. Formulations in the form of dusts and granules and also sprayable solutions are not diluted further with other inert substances before use. The application rate required varies with the external conditions, such as temperature, humidity and the like, in general, it is between 0.01 and 10 kg of active compound per hectare, preferably about 0.1 to 5.0 kg per hectare.

For some fields of use it can be expedient to use the new herbicides together with one or more herbicides, for example as a tank mixture or in the form of a finished formulation, in order to achieve further advantageous effects.

The active compounds according to the invention can be combined with other herbicides, insecticides and fungicides.

Concentrations between 0.01 and 1.25 kg per hectare are suitable for use as growth regulators. It is preferable to use aqueous dispersions of wettable powders or dilutions of emulsifiable concentrates. Application is made by the post-emergence technique. Preferred crops are maize and tobacco.

PREPARATION EXAMPLES

Example 1

2,3-Dihydro-6,8-dimethyl-3-oxopyrimidino-[1,2-b][1,2,4,6]-thiatriazine 1,1-dioxide 17.5 ml (0.2 mol) of chlorosulfonyl isocyanate (CSI) are dissolved in 300 ml of anhydrous $CH_3CN$, and 24.6 g (0.2 mol) of 2-amino-4,6-dimethylpyrimidine are added at $-40°$ C., under nitrogen, in the course of approx. 5 minutes. After the cooling bath has been removed, the reaction mixture is allowed to reach 10° C. in the course of approx. 1.5 hours (the contents of the flask take on a deep red coloration above $-5°$ C.). After stirring for a further 18 hours at room temperature the precipitate is filtered off with suction, washed with $CH_3CN$ and then with N-hexane and dried at 60° C. in a high vacuum. 21.5 g (42.2% of theory) of 2,3-dihydroxo-6,5-dimethyl-3-oxopyrimidino-[1,2-b][1,2,4,6]thiatriazine 1,1-dioxide are obtained, melting point 240° C. (decomposition).

The compounds of the formula (II) indicated in the table below are obtained analogously.

| Example No. | R$_5$ (or R$_6$) | R$_6$ (or R$_5$) | Y | Physical data |
|---|---|---|---|---|
| 2 | CH$_3$ | OCH$_3$ | CH | M.p. 294–297° C. |
| 3 | CH$_3$ | H | CH | |
| 4 | CH$_3$ | Cl | CH | M.p. 271° C. (decomp.) |
| 5 | OCH$_3$ | OCH$_3$ | CH | M.p. 272–6° C. |
| 6 | CH$_3$ | OC$_2$H$_5$ | CH | |
| 7 | C$_2$H$_5$ | OCH$_3$ | CH | |
| 8 | CH$_2$SCH$_3$ | OCH$_3$ | CH | |
| 9 | CH$_2$OCH$_3$ | OCH$_3$ | CH | M.p. 186° C. (decomp.) |
| 10 | CH$_3$ | OCH$_3$ | N | |
| 11 | OCH$_3$ | OCH$_3$ | N | |
| 12 | CH$_2$Cl | OCH$_3$ | N | |
| 13 | CH$_2$OCH$_3$ | OCH$_3$ | N | |
| 14 | OC$_2$H$_5$ | CH$_3$ | N | |
| 15 | C$_2$H$_5$ | OCH$_3$ | N | |
| 16 | CH$_2$SCH$_3$ | OCH$_3$ | N | |

The compounds of Examples 2–16 are in the form of mixtures of isomers.

Example 17

1-[(N-methoxy-N-methylamino)-sulfonyl]-3-(4-methoxy-6-methyl-2-pyrimidinyl)-urea 14.8 g (0.105 mol) of CSI are dissolved in 150 ml of methylene dichloride at −70° C., under nitrogen, and 13.9 g (0.1 mol) of 2-amino-4-methoxy-6-methylpyrimidine are added in portions.

The reaction mixture is allowed to reach 0° C. in the course of one hour and is then cooled to −70° C., 9.35 g (0.1 mol) of O,N-dimethylhydroxylamine hydrochloride are added and 20.2 g (0.2 mol) of triethylamine—dissolved in 100 ml of methylene dichloride—are added to the mixture in the course of a further hour. After being stirred for 2 hours at −70° C., the mixture is stirred for a further 18 hours at room temperature and is washed with 0.5 N sodium acetate solution and then with saturated sodium chloride solution, and the methylene dichloride phase is dried over sodium sulfate. After the dropwise addition of n-hexane, 19.8 g (55.3% of theory) of 1-[(N-methoxy-N-methylamino)-sulfonyl]-3-(4-methoxy-6-methyl-2-pyrimidinyl)-urea of melting point 154° C. are obtained.

Example 18

1-[(N-methoxy-N-methylamino)-sulfonyl]-3-(4,6-dimethyl-2-pyrimidinyl)-urea 5.7 g (0.025 mol) of 2,3-dihydro-6,8-dimethyl-3-oxopyrimidino-[1,2-b][1,2,4,6]-thiatriazine 1,1-dioxide (cf. Example 1) are suspended in 100 ml of methylene dichloride, and 3.05 g (0.05 mol) of O,N-dimethylhydroxylamine—dissolved in 50 ml of methylene dichloride—are added at −40° C. in the course of one hour. The mixture is stirred for a further 18 hours at room temperature and evaporated to dryness, and the residue is taken up in water and acidified to pH 4–5 with 0.5 N HCl. After extraction with methylene dichloride, the mixture is worked up as under Example 17. 4.9 g (67.8% of theory) of 1-[(N-methoxy-N-methylamino)-sulfonyl]-3-(4,6-dimethyl-2-pyrimidinyl)-urea of melting point 152° C. are obtained.

Example 19

1-[(N-methylsulfonyl-N-methylamino)-sulfonyl]-3-(4-methoxy-6-methyl-2-pyrimidinyl)-urea 13.9 g (0.1 mol) of 2-amino-4-methoxy-6-methylpyrimidine are suspended in 150 ml of methylene dichloride, and 21.4 g (0.1 mol) of N-methylsulfonyl isocyanate in 50 ml of methylene dichloride are added at 0° C. in the course of one hour. Stirring is continued for 15 hours at room temperature and the product is then precipitated with n-hexane. 20.4 g (58% of theory) of 1-[(N-methylsulfonyl-N-methylamino)-sulfonyl]-3-(4-methoxy-6-methyl-2-pyrimidinyl)-urea of melting point 118°–120° C. are obtained.

The compounds of the formula I listed in Table 2 below can be synthesized analogously in accordance with any one of Examples 17 to 19.

TABLE 2

| Example No. | R$_1$ | X | R$_2$ | R$_3$ | R$_4$ | R$_5$ | R$_6$ | Y | M.p. |
|---|---|---|---|---|---|---|---|---|---|
| 20 | CH$_3$ | O | CH$_3$ | H | H | OCH$_3$ | OCH$_3$ | CH | 166–168 |
| 21 | CH$_3$ | O | H | H | H | CH$_3$ | CH$_3$ | CH | 165 |
| 22 | CH$_3$ | O | H | H | H | OCH$_3$ | CH$_3$ | CH | |
| 23 | CH$_3$ | O | H | H | H | OCH$_3$ | OCH$_3$ | CH | |
| 24 | C$_2$H$_5$ | O | H | H | H | CH$_3$ | CH$_3$ | CH | |
| 25 | C$_2$H$_5$ | O | H | H | H | OCH$_3$ | CH$_3$ | CH | |
| 26 | C$_2$H$_5$ | O | H | H | H | OCH$_3$ | OCH$_3$ | CH | |
| 27 | C$_2$H$_5$ | O | CH$_3$ | H | H | CH$_3$ | CH$_3$ | CH | |
| 28 | C$_2$H$_5$ | O | CH$_3$ | H | H | OCH$_3$ | CH$_3$ | CH | |
| 29 | C$_2$H$_5$ | O | CH$_3$ | H | H | OCH$_3$ | OCH$_3$ | CH | |
| 30 | nC$_3$H$_7$ | O | CH$_3$ | H | H | CH$_3$ | CH$_3$ | CH | Resin |
| 31 | nC$_3$H$_7$ | O | CH$_3$ | H | CH$_3$ | CH$_3$ | CH$_3$ | CH | |
| 32 | nC$_3$H$_7$ | O | CH$_3$ | H | H | OCH$_3$ | CH$_3$ | CH | |
| 33 | isoC$_3$H$_7$ | O | CH$_3$ | H | H | CH$_3$ | CH$_3$ | CH | |
| 34 | isoC$_3$H$_7$ | O | CH$_3$ | H | H | OCH$_3$ | CH$_3$ | CH | |
| 35 | isoC$_3$H$_7$ | O | CH$_3$ | H | H | OCH$_3$ | OCH$_3$ | CH | |
| 36 | CH$_2$=CHCH$_2$ | O | CH$_3$ | H | H | CH$_3$ | CH$_3$ | CH | 126 |
| 37 | CH$_2$=CHCH$_2$ | O | CH$_3$ | H | H | OCH$_3$ | CH$_3$ | CH | |
| 38 | CH$_2$=CH—CH$_2$ | O | CH$_3$ | H | H | OCH$_3$ | OCH$_3$ | CH | |
| 39 | CH$_2$=CH—CH$_2$ | O | CH$_3$ | H | H | Cl | CH$_3$ | CH | |
| 40 | CH$_2$=CHCH$_2$ | O | CH$_3$ | H | H | CH$_2$SCH$_3$ | OCH$_3$ | CH | |
| 41 | CH$_2$=CHCH$_2$ | O | CH$_3$ | H | H | CH$_2$OCH$_3$ | CH$_3$ | CH | |
| 42 | CH$_3$CH$_2$CH$_2$CH$_2$ | O | CH$_3$ | H | H | CH$_3$ | CH$_3$ | CH | 100 |
| 43 | CH$_3$CH$_2$CH$_2$CH$_2$ | O | CH$_3$ | H | H | OCH$_3$ | CH$_3$ | CH | |
| 44 | CH$_3$CH$_2$CH$_2$CH$_2$ | O | CH$_3$ | H | H | OCH$_3$ | OCH$_3$ | CH | |
| 45 | CH$_3$CH$_2$CH(—)CH$_3$ | O | CH$_3$ | H | H | CH$_3$ | CH$_3$ | CH | |

TABLE 2-continued

| Example No. | R₁ | X | R₂ | R₃ | R₄ | R₅ | R₆ | Y | M.p. |
|---|---|---|---|---|---|---|---|---|---|
| 46 | CH₃CH₂CH(CH₃)— | O | CH₃ | H | H | OCH₃ | CH₃ | CH | |
| 47 | CH₃ | O | C₂H₅ | H | H | CH₃ | CH₃ | CH | |
| 48 | CH₃ | O | C₂H₅ | H | H | OCH₃ | CH₃ | CH | |
| 49 | CH₃ | O | C₂H₅ | H | H | OCH₃ | OCH₃ | CH | |
| 50 | CH₃ | O | CH₂CH₂CH₃ | H | H | CH₃ | CH₃ | CH | |
| 51 | CH₃ | O | CH₂CH₂CH₃ | H | H | OCH₃ | CH₃ | CH | |
| 52 | CH₃ | O | CH(CH₃)₂ | H | H | OCH₃ | CH₃ | CH | |
| 53 | C₂H₅ | O | CH(CH₃)₂ | H | H | OCH₃ | OCH₃ | CH | |
| 54 | CH₃ | O | H | H | H | OCH₃ | CH₃ | N | |
| 55 | CH₃ | O | CH₃ | H | H | OCH₃ | CH₃ | N | 172 |
| 56 | CH₃ | O | CH₃ | H | H | OCH₃ | OCH₃ | N | |
| 57 | C₂H₅ | O | CH₃ | H | H | CH₃ | OCH₃ | N | |
| 58 | C₂H₅ | O | CH₃ | H | H | OCH₃ | OCH₃ | N | |
| 59 | C₂H₅ | O | CH₃ | H | H | CH₂Cl | OCH₃ | N | |
| 60 | C₂H₅ | O | CH₃ | H | H | CH₂OCH₃ | OCH₃ | N | |
| 61 | C₂H₅ | O | CH₃ | H | H | CH(OCH₃)₂ | OCH₃ | N | |
| 62 | C₂H₅ | O | CH₃ | H | H | CH₂SCH₃ | OCH₃ | N | |
| 63 | C₂H₅ | O | CH₃ | H | H | N(CH₃)₂ | OCH₃ | N | |
| 64 | C₂H₅ | O | CH₃ | H | H | OCH₂CH₃ | OCH₃ | N | |
| 65 | CH₂CH₂CH₃ | O | CH₃ | H | H | OCH₃ | CH₃ | N | |
| 66 | CH₂CH₂CH₃ | O | CH₃ | H | H | OCH₃ | OCH₃ | N | |
| 67 | CH₂=CH—CH₂ | O | CH₃ | H | H | OCH₃ | OCH₃ | N | |
| 68 | CH₂=CH—CH₂ | O | CH₃ | H | H | OCH₃ | OCH₃ | N | |
| 69 | CH₃CH₂CH₂CH₂ | O | CH₃ | CH₃ | CH₃ | OCH₃ | CH₃ | N | |
| 70 | CH₃CH₂CH₂CH₂ | O | C₂H₅ | H | H | N(CH₃)₂ | OCH₃ | N | |
| 71 | CH₃ | SO₂ | H | H | H | CH₃ | CH₃ | CH | |
| 72 | CH₃ | SO₂ | CH₃ | H | H | CH₃ | CH₃ | CH | 148–150 |
| 73 | CH₃ | SO₂ | CH₃ | H | H | OCH₃ | OCH₃ | CH | 175–177 |
| 74 | CH₃ | SO₂ | C₂H₅ | H | H | CH₃ | CH₃ | CH | |
| 75 | CH₃ | SO₂ | C₂H₅ | H | H | OCH₃ | CH₃ | CH | |
| 76 | CH₃ | SO₂ | C₂H₅ | H | H | OCH₃ | OCH₃ | CH | |
| 77 | CH₃ | SO₂ | CH₃CH₂CH₂ | H | H | CH₃ | CH₃ | CH | 148–150 |
| 78 | CH₃ | SO₂ | CH₃CH₂CH₂ | H | H | OCH₃ | CH₃ | CH | 140–142 |
| 79 | CH₃ | SO₂ | CH₂=CHCH₂ | H | H | CH₃ | CH₃ | CH | 137–141 |
| 80 | CH₃ | SO₂ | CH₂=CHCH₂ | H | H | OCH₃ | CH₃ | CH | 158–160 |
| 81 | CH₃ | SO₂ | CH₂=CHCH₂ | H | H | Cl | CH₃ | CH | |
| 82 | CH₃ | SO₂ | CH₂=CHCH₂ | H | H | CH₂OCH₃ | CH₃ | CH | |
| 83 | CH₃ | SO₂ | CH₂=CHCH₂ | H | H | CH₂OCH₃ | OCH₃ | CH | |
| 84 | CH₃ | SO₂ | CH₂=CHCH₂ | H | H | CH₂SCH₃ | OCH₃ | CH | |
| 85 | CH₃ | SO₂ | CH₂=CHCH₂ | H | H | N(CH₃)₂ | CH₃ | CH | |
| 86 | CH₃ | SO₂ | CH(CH₃)₂ | H | H | CH₃ | CH₃ | CH | |
| 87 | CH₃ | SO₂ | CH(CH₃)₂ | H | H | OCH₃ | CH₃ | CH | 160–62 |
| 88 | ClCH₂ | SO₂ | CH₃ | H | H | CH₃ | CH₃ | CH | 144–146 |
| 89 | ClCH₂ | SO₂ | CH₃ | H | H | OCH₃ | CH₃ | CH | |
| 90 | ClCH₂ | SO₂ | CH₃ | H | H | OCH₃ | OCH₃ | CH | |
| 91 | ClCH₂ | SO₂ | CH₃ | H | H | CH(OC₂H₅)₂ | OCH₃ | CH | |
| 92 | CF₂H | SO₂ | CH₃ | H | H | CH₃ | CH₃ | CH | Resin |
| 93 | CF₂H | SO₂ | CH₃ | H | H | OCH₃ | CH₃ | CH | Resin |
| 94 | CF₃ | SO₂ | CH₃ | H | H | CH₃ | CH₃ | CH | |
| 95 | CF₃ | SO₂ | CH₃ | H | H | OCH₃ | CH₃ | CH | |
| 96 | CHF₂CF₂ | SO₂ | CH₃ | H | H | CH₃ | CH₃ | CH | |
| 97 | CHF₂CF₂ | SO₂ | CH₃ | H | H | OCH₃ | CH₃ | CH | |
| 98 | FCH₂ | SO₂ | CH₃ | H | H | CH₃ | CH₃ | CH | |
| 99 | FCH₂ | SO₂ | CH₃ | H | H | OCH₃ | CH₃ | CH | |
| 100 | CH₃ | SO₂ | CH₃ | H | H | OCH₃ | CH₃ | N | 72–78 |

TABLE 2-continued

| Example No. | $R_1$ | X | $R_2$ | $R_3$ | $R_4$ | $R_5$ | $R_6$ | Y | M.p. |
|---|---|---|---|---|---|---|---|---|---|
| 101 | $CH_3$ | $SO_2$ | $CH_3$ | H | H | $OC_2H_5$ | $CH_3$ | N | 77–83 |
| 102 | $ClCH_2$ | $SO_2$ | $CH_3$ | H | H | $OCH_3$ | $CH_3$ | N | 125–128 |
| 103 | $ClCH_2$ | $SO_2$ | $CH_3$ | H | H | $SCH_3$ | $CH_3$ | N | 135–136 |
| 104 | $CH_3$ | $SO_2$ | $CH_2=CHCH_2$ | H | H | $SCH_3$ | $CH_3$ | N | 116–118 |
| 105 | $CH_3$ | $SO_2$ | $CH_2=CHCH_2$ | H | H | $OCH_3$ | $CH_3$ | N | 132–133 |
| 106 | $CH_3$ | $SO_2$ | $CH_3CH_2CH_2$ | H | H | $OCH_3$ | $CH_3$ | N | 98–99 |
| 107 | $CH_3$ | $SO_2$ | $CH_3CH_2CH_2$ | H | H | $OCH_3$ | $OCH_3$ | N | 128–130 |
| 108 | $C_2H_5$ | $SO_2$ | $CH_3$ | H | H | $OCH_3$ | $CH_3$ | N | |
| 109 | $C_3H_7$ | $SO_2$ | $CH_3$ | H | H | $OCH_3$ | $CH_3$ | N | |
| 110 | $CH_2=CH-$ | $SO_2$ | $CH_3$ | H | H | $OCH_3$ | $CH_3$ | N | |
| 111 | $CH\equiv C-CH_2-$ | $SO_2$ | $CH_3$ | H | H | $OCH_3$ | $CH_3$ | N | |
| 112 | $CH\equiv C-CH_2-$ | $SO_2$ | $CH_3$ | H | H | $OCH_3$ | $OCH_3$ | N | |
| 113 | $CF_3$ | $SO_2$ | $CH_3$ | H | H | $OCH_3$ | $CH_3$ | N | |
| 114 | $CHF_2$ | $SO_2$ | $CH_3$ | H | H | $OCH_3$ | $CH_3$ | N | |
| 115 | $CHF_2$ | $SO_2$ | $CH_3$ | H | H | $OCH_3$ | $OCH_3$ | N | |
| 116 | $CH_2F$ | $SO_2$ | $CH_3$ | H | H | $OCH_3$ | $CH_3$ | N | |
| 117 | $CHF_2CF_2$ | $SO_2$ | $CH_3$ | H | H | $OCH_3$ | $CH_3$ | N | |
| 118 | $CF_3CHFCF_2$ | $SO_2$ | $CH_3$ | H | H | $OCH_3$ | $CH_3$ | N | |
| 119 | $CHF_2$ | $SO_2$ | $C_2H_5$ | H | H | $OCH_3$ | $OCH_3$ | N | |
| 120 | $CHF_2$ | $SO_2$ | $CH_3$ | $CH_3$ | H | $OCH_3$ | $CH_3$ | N | |
| 121 | $CHF_2$ | $SO_2$ | $CH_3$ | H | $CH_3$ | $OCH_3$ | $OCH_3$ | N | |
| 122 | $CH_3$ | $SO_2$ | $CH_3CH_2CH_2$ | H | H | $OCH_3$ | $OCH_3$ | CH | 150–153 |
| 123 | $CH_3$ | $SO_2$ | $CH(CH_3)_2$ | H | H | $OCH_3$ | $OCH_3$ | CH | 120–122 |
| 124 | $CH_3$ | $SO_2$ | $CH(CH_3)-$ | H | H | Cl | $OCH_3$ | CH | 182–184 |

HERBICIDAL ACTION

The present compounds according to the invention exhibit an excellent herbicidal activity against a broad spectrum of economically important monocotyledonous and dicotyledonous weeds. Even perennial root-propagated weeds which are difficult to control are dealt with throughly by the active compounds. It is immaterial in this respect whether the substances are applied by pre-sowing, pre-emergence or post-emergence spraying.

If the compounds according to the invention are applied to the surface of the soil by the pre-sowing or pre-emergence technique before the weed plants have germinated, the emergence of the seedlings is not prevented. The weeds grow up to the cotyledon stage, but then cease their growth and finally wither completely after 3–5 weeks. If the active compounds are applied by the post-emergence technique to the green parts of the plants, a drastic cessation of growth also sets in very rapidly after the treatment, and the weed plants remain in the stage of growth existing at the time of application or wither completely after a certain time, so that weed competition harmful to the crop plants can be eliminated very soon and for an extended period by the use of the novel agents according to the invention.

Although the compounds according to the invention exhibit an excellent herbicidal activity against monocotyledonous and dicotyledonous weeds, cultivated plants of economically important crops, such as, for example, wheat, barley, rye, rice, maize, sugar-beet, cotton and soya, are only damaged insubstantially or not at all. Compared with the state of the art, the present substances according to the invention therefore have a substantially improved selectivity for crop plants.

For these reasons, the present compounds are very suitable for controlling undesirable plant growth in agricultural crop plantations.

The damage caused to the weed plants or the toleration by crop plants has been assessed in a code from 0 to 5. The numbers in this code have the following meanings:

0=no action (damage)
1=0–20% action
2=20–40% action
3=40–60% action
4=60–80% action
5=80–100% action 1. Pre-emergence technique Seeds or pieces of rhizome of monocotyledonous and dicotyledonous weeds were laid out in loam soil in plastic pots ($\phi$9 cm) and were covered with soil. The compounds according to the invention, formulated as wettable powders or as emulsion concentrates, were applied to the surface of the soil in the form of aqueous suspensions or emulsions. The amount of water applied per pot was equivalent to 600–800 liters per hectare. After the treatment, the test pots were placed in a greenhouse and the test plants were cultivated under good conditions for growth (temperature: 23°±1° C.; relative humidity 60–80%). After approx. 3 weeks the damage to the plants was assessed visually. Untreated controls were used as a comparison. The pre-emergence results are listed in Tables 1 and 3.

The test results shown prove the excellent herbicidal pre-emergence action of the new compounds, according to the invention, against grasslike weeds and weeds.

2. Post-emergence technique

Seeds of monocotyledonous and dicotyledonous weeds were sown in pots and cultivated under good conditions for growth in a greenhouse. The test plants were treated in the three-leaf stage, 3 weeks after being sown. The preparations according to the invention, formulated as wettable powders or as emulsion concentrates, were sprayed on the green parts of the plants in various dosages, and the action of the preparations was assessed visually in comparison with untreated controls after a holding time of approx. 3 weeks in the greenhouse under optimum conditions for growth (temperature: 23°±1° C.; relative humidity 60–80%). The agents according to the invention exhibited a good herbicidal activity against a broad spectrum of economically important annual and perennial weeds and grasslike weeds (Tables 3 and 4).

Abbreviations:
a.i.=active ingredient

STM=*Stellaria media*
AMR=*Amaranthus retroflexus*
SIA=*Sinapis arvensis*
LOM=*Lolium multiflorum*
ECG=*Echinochloa crus-galli*
AS=*Avena sativa*.

TABLE 3

| | Herbicidal action of the heterocyclic sulfonyl-ureas when used before emergence | | | | | |
|---|---|---|---|---|---|---|
| Compound No. | Dose of a.i./hectare (kg) | Herbicidal action | | | | |
| | | STM | AMR | SIA | LOM | ECG | AS |
| 17 | 2.5 | 5 | 5 | 5 | 5 | 5 | 4 |
| 18 | 2.5 | 5 | 5 | 5 | 5 | 5 | 4 |
| 19 | 2.5 | 5 | 5 | 5 | 5 | 5 | 4 |
| 20 | 2.5 | 5 | 5 | 5 | 2 | 4 | 1 |
| 21 | 2.5 | 4 | 2 | 1 | 2 | 2 | 0 |
| 36 | 2.5 | 5 | 5 | 5 | 5 | 5 | 1 |
| 42 | 2.5 | 5 | 5 | 5 | 5 | 5 | 1 |
| 55 | 2.5 | 2 | 2 | 0 | 2 | 1 | 0 |
| 72 | 2.5 | 5 | 5 | 5 | 5 | 5 | 5 |
| 77 | 2.5 | 5 | 4 | 5 | 4 | 5 | 3 |
| 78 | 2.5 | 5 | 5 | 5 | 4 | 4 | 3 |
| 79 | 2.5 | 5 | 5 | 5 | 5 | 5 | 5 |
| 80 | 2.5 | 5 | 5 | 5 | 5 | 5 | 4 |
| 88 | 2.5 | 5 | 5 | 5 | 5 | 5 | 3 |
| 100 | 2.5 | 5 | 4 | 5 | 5 | 5 | 2 |
| 101 | 2.5 | 5 | 3 | 3 | 4 | 5 | 2 |
| 102 | 2.5 | 5 | 5 | 5 | 5 | 5 | 3 |
| 103 | 2.5 | 2 | — | — | 2 | — | — |
| 104 | 2.5 | 5 | — | — | 4 | — | — |
| 105 | 2.5 | 5 | 5 | 5 | 5 | 5 | 2 |
| 106 | 2.5 | 5 | 3 | 5 | 4 | 3 | 2 |
| 107 | 2.5 | 5 | — | — | 3 | — | — |
| 73 | 2.5 | 5 | 5 | 5 | 5 | 5 | 5 |
| 87 | 2.5 | 5 | 5 | 5 | 5 | 5 | 5 |
| 122 | 2.5 | 5 | 5 | 5 | 5 | 5 | 5 |

TABLE 4

| | Herbicidal action of the heterocyclic sulfonyl-ureas when used after emergence | | | | | |
|---|---|---|---|---|---|---|
| Compound No. | Dose of a.i./hectare (kg) | Herbicidal action | | | | |
| | | SIA | AMR | STM | AS | ECG | LOM |
| 17 | 2.5 | 5 | 5 | 4 | 2 | 4 | 4 |
| 18 | 2.5 | 5 | 5 | 5 | 4 | 5 | 5 |
| 19 | 2.5 | 5 | 5 | 5 | 4 | 5 | 5 |
| 20 | 2.5 | 5 | 5 | 5 | 0 | 2 | 3 |
| 21 | 2.5 | 4 | 0 | 3 | 0 | 0 | 1 |
| 36 | 2.5 | 4 | 4 | 4 | 2 | 4 | 4 |
| 42 | 2.5 | 4 | 5 | 5 | 5 | 3 | 3 |
| 55 | 2.5 | 3 | 0 | 2 | 1 | 0 | 2 |
| 72 | 2.5 | 5 | 5 | 5 | 5 | 5 | 5 |
| 77 | 2.5 | 5 | 5 | 4 | 2 | 4 | 4 |
| 78 | 2.5 | 5 | 5 | 5 | 2 | 4 | 3 |
| 79 | 2.5 | 5 | 5 | 5 | 3 | 5 | 4 |
| 80 | 2.5 | 5 | 5 | 5 | 2 | 5 | 3 |
| 88 | 2.5 | 5 | 5 | 5 | 4 | 5 | 5 |
| 100 | 2.5 | 5 | 5 | 4 | 2 | 5 | 4 |
| 101 | 2.5 | 5 | 5 | 5 | 1 | 5 | 4 |
| 102 | 2.5 | 5 | 5 | 5 | 1 | 4 | 3 |
| 103 | 2.5 | 3 | 4 | 3 | 0 | 2 | 1 |
| 104 | 2.5 | 5 | 5 | 4 | 1 | 3 | 3 |
| 105 | 2.5 | 4 | 5 | 4 | 2 | 5 | 3 |
| 106 | 2.5 | 5 | 5 | 5 | 1 | 5 | 3 |
| 107 | 2.5 | 5 | 5 | 5 | 2 | 4 | 3 |
| 73 | 2.5 | 5 | 5 | 5 | 5 | 5 | 5 |
| 87 | 2.5 | 5 | 4 | 5 | 5 | 5 | 5 |
| 122 | 2.5 | 5 | 5 | 5 | 5 | 5 | 5 |

We claim:
1. A compound of the formula I

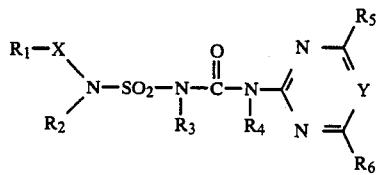

in which X is O or —SO$_2$—, Y is N, R$_1$ is a (C$_1$–C$_6$)-alkyl, (C$_2$–C$_6$)-alkenyl or (C$_2$–C$_6$)-alkinyl radical which is unsubstituted or substituted by halogen, (C$_1$–C$_4$)-alkoxy or (C$_1$–C$_4$)-alkoxycarbonyl, R$_2$ is hydrogen, (C$_1$–C$_6$)-alkyl, (C$_2$–C$_6$)-alkenyl, (C$_2$–C$_6$)-alkinyl or cyclohexyl, R$_3$ and R$_4$ independently of one another are hydrogen or (C$_1$–C$_4$)-alkyl, and R$_5$ and R$_6$ independently of one another are hydrogen, (C$_1$–C$_4$)-alkyl or (C$_1$–C$_4$)-alkoxy, said alkyl or alkoxy unsubstituted, monosubstituted or disubstituted by halogen, (C$_1$–C$_4$)-alkoxy or (C$_1$–C$_4$)-alkylthio, or are halogen, (C$_1$–C$_4$)-alkylthio, (C$_1$–C$_4$)-alkylamino or (C$_1$–C$_4$)-dialkylamino, and also, if R$_2$ and R$_3$ are hydrogen, physiologically acceptable salts thereof.

2. A compound of the formula I as claimed in claim 8, in which R$_1$ and R$_2$ independently of one another are (C$_1$–C$_3$)-alkyl or (C$_1$–C$_3$)-alkenyl, R$_3$ and R$_4$ are hydrogen, R$_5$ and R$_6$ independently of one another are (C$_1$–C$_2$)-alkyl or (C$_1$–C$_2$)-alkoxy, X is SO$_2$ and Y is N.

3. A herbicidal and growth-regulating agent which contains compounds as claimed in claim 1 and an inert carrier in a herbicidally or growth-regulating effective amount.

4. A process for controlling undesirable plant growth or for regulating plant growth, which comprises applying an effective amount of a compound as claimed in claim 1 to the plants to be treated or to the area cultivated.

* * * * *

UNITED STATES PATENT AND TRADEMARK OFFICE
CERTIFICATE OF CORRECTION

PATENT NO. : 4,718,937

DATED : January 12, 1988

INVENTOR(S) : Willms et al.

It is certified that error appears in the above-identified patent and that said Letters Patent is hereby corrected as shown below:

On the cover sheet for the patent, under heading "[75] Inventors:" after "Frankfurt am Main," add --Hermann Bieringer, Eppstein/Taunus--.

Signed and Sealed this

Sixth Day of September, 1988

Attest:

DONALD J. QUIGG

Attesting Officer      Commissioner of Patents and Trademarks